United States Patent [19]

Frankel

[11] Patent Number: 4,962,188

[45] **Date of Patent: * Oct. 9, 1990**

[54] RECOMBINANT RICIN TOXIN A CHAIN CONJUGATES

[75] Inventor: Arthur E. Frankel, Chapel, N.C.
[73] Assignee: Cetus Corporation, Emeryville, Calif.
[ * ] Notice: The portion of the term of this patent subsequent to Sep. 11, 2007 has been disclaimed.
[21] Appl. No.: 913,357
[22] Filed: Sep. 30, 1986

Related U.S. Application Data

[63] Continuation-in-part of Ser. No. 806,256, Dec. 6, 1985, abandoned.

[51] Int. Cl.[5] ...................... C07K 15/12; A61K 39/00

[52] U.S. Cl. .................................... 530/389; 530/387; 530/386; 530/390; 530/391; 530/395; 530/396; 530/397; 530/399; 530/351; 530/402; 530/403; 530/404; 530/405; 530/808; 514/885; 424/85.91; 435/69.1; 435/71.3

[58] Field of Search ............... 530/391, 351, 405, 370, 530/395–397, 399; 514/885; 424/85, 85.91; 435/69.1, 71.3

[56] References Cited

U.S. PATENT DOCUMENTS

| | | | |
|---|---|---|---|
| 4,340,535 | 7/1982 | Voisin et al. | 530/388 |
| 4,359,457 | 11/1982 | Neville et al. | 530/391 |
| 4,434,156 | 2/1984 | Trowbridge | 435/68 |
| 4,504,586 | 3/1985 | Nicolson | 436/548 |
| 4,522,918 | 6/1985 | Schlom et al. | 435/68 |
| 4,545,985 | 10/1985 | Pastan et al. | 424/85 |
| 4,675,382 | 6/1987 | Murphy | 530/324 |
| 4,806,494 | 2/1989 | Pastan et al. | 424/85.91 |

FOREIGN PATENT DOCUMENTS

| | | | |
|---|---|---|---|
| 0145111 | 6/1985 | European Pat. Off. | 435/68 |

OTHER PUBLICATIONS

Foxwall et al., *Biochemica et Biophy. Acta 840, 1985, pp. 193–203.*

Roberts et al., *JBC* 268, 1985, pp. 15682–15686.

Butterworth et al., *Eur. J. Biochem.* 137, 1985, pp. 57–65.

Leonard et al., *Cancer Res.* 45, 1985, pp. 5263–6269.

Shimoda et al., *Agric. Biol. Chem.* 49(4), 1985, pp. 1175–1180.

Simeral et al., *JBC* 255, 1980, pp. 11098–11101.

Thorpe et al., *Eur. J. Biochem.* 140, 1984, pp. 63–71.

Bourne et al., *Eur. J. Biochem.* 155, 1986, pp. 1–10.

Skilleter et al., *FEBS* 196(2), 2/1986, pp. 344–348.

Vitetta et al., *Cancer Drug Delivery* 2(3), 1985, pp. 191–198.

Thorpe et al., *Eur. J. Biochem.* 147, 1985, pp. 197–206.

Herschman, *Biochem. Biophys. Res. Comm.* 1984, pp. 551–557, vol. 124(2).

Shimizu et al., C.A. vol. 402, 1985, p. 161, #73836m.

Roth et al., *JBC* 256(11), 1981, pp. 5350–5354.

Oeltmann et al., *JBC* 254(4), 1979, pp. 1028–1032.

Raso et al., *Cancer Res.*, vol. 41, 1981, pp. 2073–2078.

Masuho et al., *J. Biochem.*, 91, 1982, pp. 1583–1591.

Lamb et al., *Eur. J. Biochem.* 148, 1985, pp. 265–270.

Funatsu et al., Agri. Biol. Chem. 43(10), 1979, pp. 2221–2224.

Greenfield et al., *PNAS* 80, 1983, pp. 6853–6857.

Whiteley et al., CA vol. 103, 1985, p. 191, #154993h.

Morimoto et al., *J. Immunol.* 131(4), 1983, pp. 1762–1764.

Chang et al., *JBC* 252(4), 1977, pp. 1515–1522.

Diener et al., *Science* 231, 1986, pp. 148–150.

Bjorn, J. J. et al., Cancer Research vol. 45, pp. 1214–1221 (1985).

Pirker R., 1986 AACR Abstract.

Pirker, R. et al., J. Clin. Invest., vol. 76, pp. 1261–1267 (1985).

Pirker R. et al., Cancer Research, vol. 45, pp. 751–757 (1985).

Hamilton T. C. et al., Cancer Research, vol. 43, pp. 5379–5389 (1983).

Hamilton T. C., et al., Cancer Research, vol. 44, pp. 5286–5290 (1984).

*Primary Examiner*—Garnette Draper

*Attorney, Agent, or Firm*—Gregory J. Giotta; Elliott L. Fineman; Albert P. Halluin

[57] ABSTRACT

Conjugates comprising recombinant ricin toxin A chain and a binding moiety which may be an antigen binding portion selected from the group consisting of Fab, Fab′ and $F(ab')_2$ fragments of monoclonal or polyclonal antibodies, hormones, lectins or other compounds that are recognized by cell receptors, are described and claimed.

2 Claims, 2 Drawing Sheets

4,962,188

RECOMBINANT RICIN TOXIN A CHAIN CONJUGATES

This application is a continuation-in-part application of U.S. Patent Application Ser. No. 806,256 filed Dec. 6, 1985, now abandoned.

TECHNICAL FIELD

This invention is in the fields of immunology and cancer diagnosis and therapy. More particularly it concerns rurine monoclonal antibodies active against human ovarian cancer, hybridomas that produce those antibodies, immunochemicals made from those antibodies, and diagnostic and therapeutic methods that use those imrunochemicals. The invention also concerns conjugates of recombinant ricin toxin A chain.

BACKGROUND ART

Among gynecological malignancies occurring in American women, ovarian cancer most frequently causes death. The malignancy remains confined to the peritoneal cavity during practically its entire clinical course. Characteristically the tumor disseminates throughout the peritoneal cavity producing acites and tumor foci on multiple peritoneal surfaces. The disease cannot be effectively cured surgically and chemotherapy is increasingly the primary treatment. Because ovarian tumors generally remain in the peritoneal cavity, chemotherapeutic agents may be administered systemically by intravenous injection or by direct infusion into the peritoneal cavity thus by-passing the circulatory system as the route for initially exposing the tumor to the chemotherapeutic agent.

The use of monoclonal antibodies against antigens associated with cancerqus ovarian tissues has been reported to only a limited extent. An antibody to human transferrin receptor linked to Pseudomonas exotoxin has been reported to have cytotoxic activity in certain human ovarian cell lines. Pirker et al., "Anti-transferrin receptor antibody linked to Pseudomonas exotoxin; a model imrunotoxin in human ovarian carcinoma cell lines", Cancer Res. 45:751–757 (1985). Anti-transferrin monoclonal antibodies that inhibit the binding of transferrin to the transferrin receptor are the subject of U.S. Pat. No. 4,434,156. The anti-transferrin monoclonal antibodies of the present invention are different from those disclosed in U.S. Pat. No. 4,434,156. Although the anti-transferrin antibody of the present invention binds the transferrin receptor, it does not inhibit the binding of transferrin to the transferrin receptor. Schlom et al., U.S. Pat. No. 4,522,918 discloses a method of producing monoclonal antibodies against certain human breast cancer tumors using soluble extracts of human breast cancer.

A principal aspect of the invention concerns murine monoclonal antibodies that:

(a) bind human ovarian cancer tissue frozen sections;
(b) are IgGs or IgMs;
(c) when bound to a cytotoxic moiety, have an $ID_{50}$ of 10 nM or less against at least one ovarian cancer cell line selected from the group consisting of OVCAR-2, OVCAR-3, OVCAR-4, OVCAR-5 or A1847; or
when bound to a cytotoxic moiety extend the survival time of mammals carrying human ovarian tumors; or when bound to a cytotoxic protein retard the rate of growth of human ovarian tumors carried by such mammals.

Preferred embodiments of these antibodies are those designated 2G3, 9C6, 33F8, 44B2, 44F4, 120H7, 200F9, 204F4, 219F3, 245E7, 260F9, 266B2, 280D11, 317G5, 369F10, 388D4, 421E8, 451C3, 454A12, 454C11, 650E2, 788G6, 871E3, and functional equivalents thereof.

The rurine x murine hybridomas i.e., hybridomas prepared from spleenocytes of immunized mice and a murine tumor partner such as a murine myeloma that produce the above described antibodies and progeny of those hybridomas are other aspects of the invention.

Another aspect of the invention relates to immunotoxins that are conjugates of (a) the above described monoclonal antibodies, and
(b) a cytotoxic moiety.

Another aspect of the invention concerns methods of extending the survival time of mammals bearing human ovarian tumor cells by administering to such mammal an amount of an immunotoxin described above effective to extend the life of such mammal.

Yet another aspect of the invention concerns methods of killing human ovarian tumor cells by contacting such cells with a cytocidally effective amount of the immunotoxin described above.

A further aspect of the invention concerns methods of retarding the rate of growth of human ovarian tumor cells carried by a mammal by administering to such mammal a tumor cell growth-retarding amount of the imaunotoxin described above.

The invention also relates to conjugates comprising recombinant ricin toxin A chain and a target cell binding moiety or "surogate B moiety".

MODES FOR CARRYING OUT THE INVENTION

Figure 1:
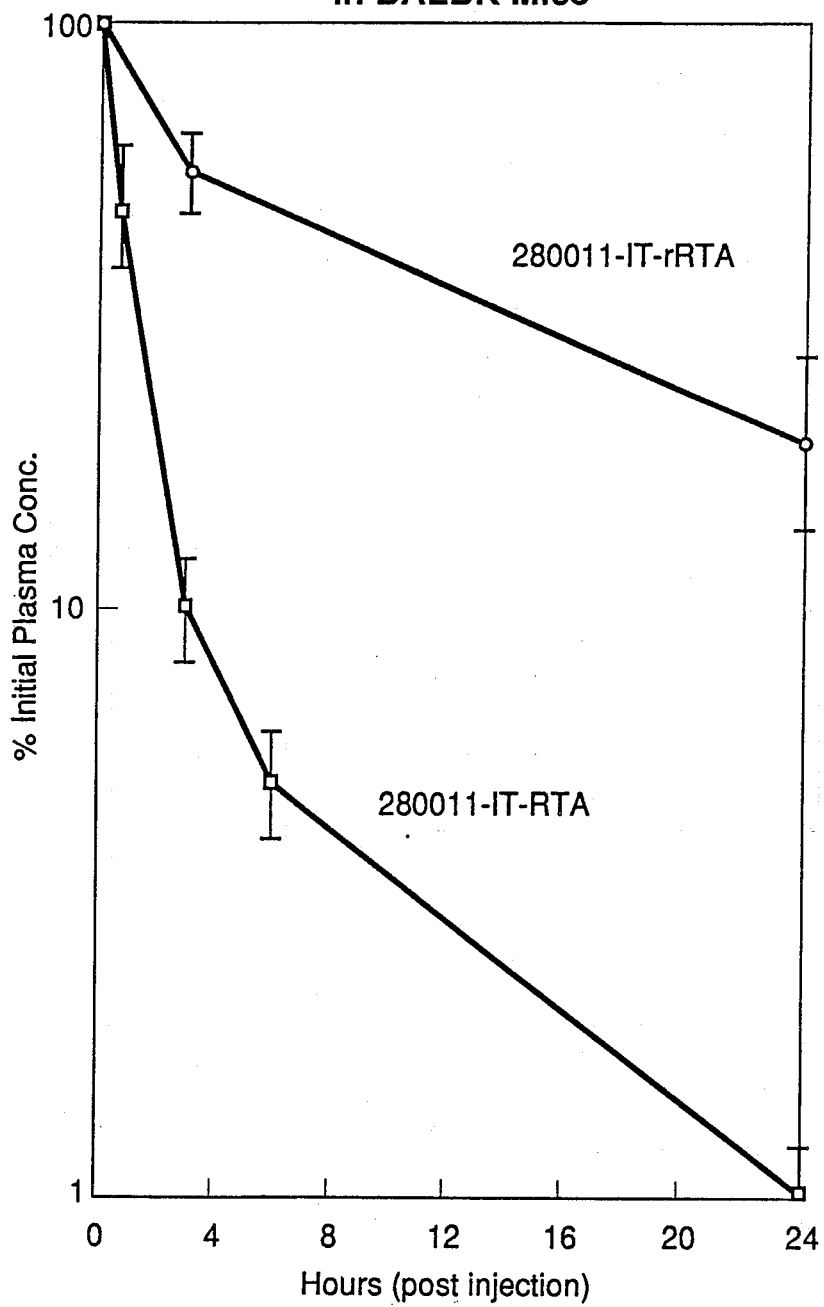
FIG. 1 is a graph of the clearance of RTA and rRTA conjugates from the serum of Balb/c mice and shows the percent of initial conjugate remaining in the serum as a function of time.
Figure 2:
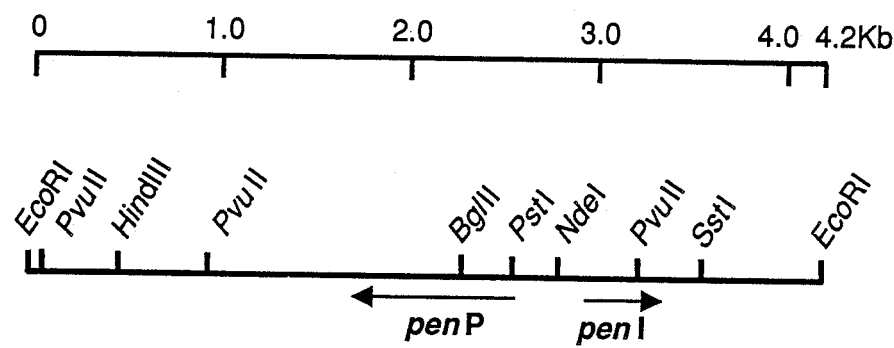

As used herein, the term "monoclonal antibody"-means an antibody composition having a homogeneous antibody population. It is not intended to be limited as regards the source of the antibody or the manner in which it is made.

As used herein the term "antigen binding portion of a monoclonal antibody" means the portion of the monoclonal antibody that binds an antigen to which the monoclonal antibody is specific. In general, such antibody binding portions of the monoclonal encompass the Fab, Fab, and F(ab')2 regions or fragments of the imrunoglobin molecule. Fab, Fab' and F(ab')2 regions of an immunoglobin may be generated by enzymatic digestion of the monoclonal antibodies using techniques well known to those skilled in the art. Fab and FC fragments may be generated by digesting the monoclonal antibody with papain Fab' fragments may be obtained by digesting the antibody with pepsin and reductive cleavage of the fragment so produced with a reducing agent. In the absence of reductive cleavage, enzymatic digestion of the monoclonal with pepsin produces F(ab')2 fragments.

As used herein with regard to the monoclonal antibodyproducing hybridomas of the invention, the term "progeny" is intended to include all derivatives, issue, and offspring of the parent hybridoma that produce the monoclonal anti-human ovarian cancer antibody produced by the parent, regardless of generation or karyotypic identity.

As used herein with respect to the exemplified rurine monoclonal antibodies against human ovarian cancer, the term "functional equivalent" means a monoclonal antibody that: (a) binds to the same antigen or epitope as an exemplified monoclonal antibody as determined by imaunoprecipitation or sandwich assay; (b) binds human ovarian cancer tissue frozen sections; (c) has a selectivity equal to or less than 0.11; (d) has a G or M isotype, and (e) when conjugated to a cytotoxic moiety forms an imrunotoxin which (i) extends the survival of a mammal bearing human ovarian cancer cells when administered to such mammal or (ii) retards the growth of human ovarian cells in a mammal bearing such cells when administered to such a mammal or (iii) is cytotoxic to human ovarian cancer cells when such cells are contacted with the immunotoxin.

As described above, the term "functional equivalent" as used herein includes five criteria. The first of these criteria, binding to the same antigen or epitope as an exemplified monoclonal antibody may be demonstrated by experiments which show crossblocking of an exemplified monoclonal antibody by the functionally equivalent monoclonal antibody. Crossblocking occurs as a result of an antibody binding to the same epitope on an antigen as that bound by one of the exemplified antibodies, or as a result of an antibody binding to a different epitope which is so closely situated on the same antigen that binding of an antibody to one epitope blocks the binding of an antibody to the second epitope. Crossblocking thus is one of the criteria by which one can determine that a functionally equivalent monoclonal antibody binds to the same antigen or epitope as an exerplified monoclonal antibody.

So-called "sandwich" assays are another method for determining whether an antibody binds the same antigen or epitope. In these assays, a first monoclonal antibody is bound to a support, for example, the surface of a titre plate well. After treatment to prevent nonspecific binding, a highly solubilized antigen preparation is added to the bound antibody. Subsequently, a second antibody, having a detectable label, for example, a fluorescent dye, is added. If the second antibody binds to the antigen, a different epitope specificity or multiple copies of the same epitope on the same antigen is indicated. If the second antibody fails to bind, either the same epitope specificity or different antigen specificity is indicated. The results of both the crossblocking and sandwich assay are further defined by a second series of tests such as immune precipitation or Western blotting to show that the antigen bound by both antibodies has the same molecular weight.

The immunotoxins according to the invention are conjugates of the monoclonal antibody and a cytotoxic moiety. The cytotoxic moiety of the immunotoxin may be a cytotoxic drug or an enzymatically active toxin of bacterial, fungal or plant origin, or an enzymatically active polypeptide chain or fragment. ("A chain") of such a toxin. Enzymatically active toxins and fragments thereof are preferred and are exemplified by diphtheria toxin A fragment, nonbinding active fragments of diphtheria toxin, exotoxin A (from *Pseudomonas aeruginosa*), ricin A chain, abrin A chain, modeccin A chain, alphasarcin, certain *Aleurites fordii* proteins, certain Dianthin proteins, *Phytolacca americana* proteins (PAP, PAPII and PAP-S), *Momordica charantia* inhibitor, curcin, crotin, *Saponaria officinalis* inhibitor, gelonin, mitogellin, restrictocin, phenomycin, and enomycin. Ricin A chain, *Pseudomonas aeruginosa* exotoxin A and PAP are preferred.

Conjugates of the monoclonal antibody and such cytotoxic moieties may be made using a variety of bifunctional protein coupling agents. Examples of such reagents are N-succinimidyl-3-(2-pyridyldithio) propionate (SPDP), iminothiolane (IT), bifunctional derivatives of imidoesters such as dimethyl adipimidate.HCl, active esters such as disuccinimidyl suberate, aldehydes such as glutaraldehyde, bis-azido compounds such as bis(p-diazoniumbenzoyl)-ethylenediamine, diisocyanates such as tolylene 2,6-diisocyante, and bis-active fluorine compounds such as 1,5-difluoro-2,4-dinitrobenzene.

The enzymatically active polypeptide of the immunotoxins according to the invention may be recombinantly produced. Recombinantly produced ricin toxin A chain (rRTA) may be produced in accordance with the methods disclosed.in U.S. patent applications Ser. Nos. 715,934 and 653,515, both of which are abandoned which are herein incorporated by reference and are assigned to the assignee of the present invention. Recombinantly produced diphtheria toxin A chain and non-binding active fragments thereof are described in U.S. patent application Ser. Nos. 578,122, now U.S. Pat. No. 4,830,962 and 648,759 now U.S. Pat. No. 4,898,443 which are incorporated herein by reference and are assigned to the assignee of the present invention.

As used herein with respect to conjugates comprising recombinant ricin toxin A chain and "the target cell binding moiety', or "surrogate B moiety', the target cell binding moiety may be such antibodies, hormones, lectins and other compounds that are recognized by receptor on tumor cell or cell surfaces such other compounds that are recognized by receptors on tumor cells or cell surfaces also include cytokines and lymphokines, such as interleukin-2 (IL-2) and muteins thereof. Muteins as used herein means mutationally altered biologically active proteins. *Glossary of Genetics and Cytogenetics*, 4th Ed. p. 381, Springer-Verlag 1976. Specific muteins of IL-2and IFN-β, a lymphokine, are disclosed in U.S. Pat. No. 4,518,584.

The term "lymphokines" as used herein encompasses lymphocyte-produced non-immunoglobulin glycoproteins that mediate the growth or mobility of a variety of leukocytes or white blood cells. Interleukin-2is an example of such lymphokines. The term "cytokines" as used herein refers to non-immunoglobulin proteins produced by non-lymphocytic non-glandular cells such as normal macrophages, fibroblasts, keratinocytes and transformed cell lines, that act on non-inflammatory cells including osteoclasts, fibroblasts and endothelial cells, and inflammatory leukocytes such as macrophages, immunological and inflammatory processes and can contribute to the regulation of normal cell growth and differentiation. As used herein, the term CSF-1, G-CSF and G-M CSF refers to proteins that stimulate the formation of macrophage, granulocyte and marophage-granulocyte colonies from hematopoetic precursor cells respectively. D. Metcalf, The Molecular Biology and Functions of the Ganulocyte-Macrophage Colony Stimulating Factors, *Blood*, 67,2:257 (Feb. 1986). Such other compounds may include growth factors such as transferrin or epidermal growth factor, and bombeisin. An example of a growth factor would be colony stimulating factors CSF-1, G-CSF and G-M-CSF. Such "target cell binding moieties' or "surogate B moieties' confer on the recombinant ricin toxin A chain conjugate specificity for tumor cells or other target cells by replacing the native B chain of the ricin toxin molecule.

Such rRTA conjugates according to the invention have been discovered to have unique and unexpected properties as compared to the same conjugates made with RTA obtained from caster beans by conventional extraction and purification methods. The rRTA conjugates are cleared from the bloodstream of mammals at a substantially slower rate than the corresponding conjugate made with RTA. As a result, in addition to greater purity of the rRTA conjugate, by eliminating the possibility of ricin toxin B chain contamination, the rRTA conjugate has a longer life in the bloodstream of the mammal into which it has been injected and a greater likelihood of attaching to the target cell prior to removal from the mammal's ciruclation. The identity of the B chain surrogate does not affect the rate of clearance to the same degree as the nature of the ricin toxin A chain. Two different antibodies conjugated to RTA are cleared with approximately the same rapidity from the circulation, yet the different antibodies when conjugated to rRTA are both cleared from the circulation at a similar and substantially slower rate.

When used to kill human ovarian cancer cells in vitro for diagnostic purposes, the conjugates will typically be added to the cell culture medium at a concentration of at least about 10 nM. The formulation and mode of administration for in vitro use are not critical. Aqueous formulations that are compatible with the culture or perfusion medium will normally be used. Cytotoxicity may be read by conventional techniques such as dye exclusion or inhibition of colony formation in a clonogenic assay to determine the presence of an ovarian cancer tumor that is susceptible to treatment with the immunotoxin of interest.

When used in vivo for therapy, the immunotoxins are administered to the patient in therapeutically effective amounts (i.e., amounts that eliminate or reduce or retard the increase of the patient's tumor burden). They will normally be administered parenterally, preferably intraperitoneally (IP). The dose and dosage regimen will depend upon the nature of the cancer (primary or metastatic) and its population, the characteristics of the particular immunotoxin, e.g., its therapeutic index, the patient, and the patient's history. The amount of immunotoxin administered (IP) will typically be in the range of about 0.01 to about 100 mg/kg and preferably between 0.01 mg/kg and 10 mg/kg of patient weight.

For parenteral administration the immunotoxins will be formulated in a unit dosage injectable form (solution, suspension, emulsion) in association with a pharmaceutically acceptable parenteral vehicle. Such vehicles are inherently nontoxic and nontherapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The imaunotoxin will typically be formulated in such vehicles at concentrations of about 0.01 mg/ml to 100 mg/ml.

Cytotoxic radiopharmaceuticals for treating ovarian cancer may be made by conjugating high linear energy transfer (LET) emitting isotopes (e.g., Y, Pr) to the antibodies. The term "cytotoxic moiety' as used herein is intended to include such isotopes.

Monoclonal Antibody Production

The antibody-producing fusion partners that are used to make the hybridomas of this invention are generated by immunizing mice with live human breast cancer cells or membrane extracts made therefrom. The mice are inoculated intraperitoneally with an immunogenic amount of the cells or extract and then boosted with similar amounts of the immunogen. Spleens are collected from the imrunized mice a few days after the final boost and a cell suspension is prepared therefrom for use in the fusion.

Hybridomas are prepared from the splenocy.tes and a rurine tumor partner using the general somatic cell hybridization technique of Kohler, B. and Milstein, C., Nature (1975) 256:495–497 as modified by Buck, D. W., et al, In Vitro (1982) 18:377–381. Available murine myeloma lines, such as those from the Salk Institute, Cell Distribution Center, San Diego, Calif., USA, may be used in the hybridization. Basically, the technique involves fusing the tumor cells and splenocytes using a fusogen such as polyethylene glycol. After the fusion, the cells are separated from the fusion medium and grown in a selective growth medium, such as HAT medium, to eliminate unhybridized parent cells. The hybridomas are expanded, if desired, and supernatants are assayed for anti-human breast cancer activity by conventional immunoassay procedures (e.g., radioimmunoassay, enzyme imaunoassay, or fluorescence immunoassay) using the immunizing agent (breast cancer cells or membrane extract) as antigen. Positive clones are characterized further to determine whether they meet the criteria of the antibodies according to the invention.

Hybridomas that produce such antibodies may be grown in vitro or in vivo using known procedures. Preferably the hybridomas are maintained as ascites in mice. The monoclonal antibodies may be isolated from the culture media or body fluids, as the case may be, by conventional imnunoglobulin purification procedures such as ammonium sulfate precipitation, gel electrophoresis, dialysis, chromatography, and ultrafiltration, if desired.

Monoclonal Antibody Selection/Characterization

The important characteristics of the monoclonal antibodies are (1) their immunoglobulin class, (2) their ability to bind human ovarian cancer tissue, (3) their selectivity as defined further hereinbelow (4) their usefulness in making effective anti-human ovarian cancer immunotoxins which are either cytotoxic to human ovarian cancer cells, or extend the survival of mammals carrying human ovarian cancer cells, or retard the growth of human ovarian cancer cells in animals bearing such cells. The monoclonal antibodies suitable as imrunotoxins according to the invention were initially identified as monoclonal antibodies within a group of anti-breast cancer monoclonal antibodies.

In selecting the claimed antibodies, approximately 22,000 growing hybridoma cultures were initially screened against the unizing breast tumor membranes or cell line, a panel of seven normal tissue membranes, a fibroblast cell line and a breast tumor frozen section. Clones that reacted with the neoplastic materials, but not the normal materials, were identified in this initial screen and chosen for isotyping and additional screening for selectivity and range. The additional screening involved: sixteen normal tissue sections, five normal blood cell types, eleven nonbreast neoplasm sections, twenty-one breast cancer sections and fourteen breast cancer cell lines. In the additional screening, a number of monoclonal antibodies bound ovarian carcinoma tissue sections strongly but did not appear to bind to normal ovarian tissue sections.

For purposes of this patent application, specificity and selectivity are used interchangeably and are defined as the sum of the number of substructures stained in sixteen normal tissue frozen sections and the number of blood cell types bound, divided by the sum of the total number of substructures bound by any of the monoclonal antibodies in all the tissues on which the monoclonal antibodies were tested and five blood cell types tested. 123 Substructures and five blood cell types were counted in the tests. Antibodies were deemed to be appropriate candidates for ovarian cancer immunotoxin purposes if they have a selectivity equal to or less than 0.11 and bound to human ovarian cancer tissues.

Antibodies produced by one of the hybridomas were found to recognize a 200 K dalton antigen. Antibodies of two of the hybridomas bound to a 42 K dalton antigen. Four bound to one or more high molecular weight mucins (HMW) and two bound to transferrin receptors in the form of a 95 K dalton antigen. Two bound to the same epitope of a 55 K dalton antigen. All antigen weights mentioned herein were determined by sodium dodecyl sulfate (SDS) polyacrylamide gel electrophoresis under reducing conditions using procedures known in the art.

Further details of the characterization of these antibodies are provided in the examples below.

Immunochemicals

The immunochemical derivatives of this invention that are of prime importance are conjugates of the monoclonal antibodies and a cytotoxic agent.

Immunization

Fresh postsurgical human breast cancer tissue and a variety of normal tissues were used to prepare membrane extracts by homogenization and discontinuous sucrose gradient centrifugation. Human breast cancer cell lines were obtained from the Breast Cancer Task Force, the American Type Culture Collection (ATCC), and from Dr. Jorgen Fogh at Memorial Sloan Kettering. The cells were maintained and passaged as recommended by the Breast Cancer Task Force, the ATCC and Dr. Fogh. For immunizations, either membrane extract containing 100 µg of protein (Lowry assay) or ten million live breast cancer cells were inoculated intra-peritoneally into five week old Balb/c mice. The mice were boosted identically twice at monthly intervals. Three days after the last boost, the spleens were removed for cell fusion.

Hybridoma Methods

Somatic cell hybrids were prepared by the method of Buck, D. W., et al, supra, using the aurine myeloma line Sp-2/0/Ag14. All hybrodima cell lines were cloned by limiting dilution. Half of the fusions employed splenocytes from mice immunized with breast cancer membrane extracts and half used splenocytes from mice immunized with live breast cancer cell lines. Eighty-three thousand four hundred twenty-four wells were generated from those fusions, of which 22,459 exhibited hybridoma growth.

Screening Methods

Hybridoma supernatant was assayed for reactive antibody in either a solid phase enzyme-linked immunosorbent assay (ELISA) with the immunizing breast cancer membrane extract or an indirect immunofluorescence assay with the immunizing breast cancer cell line. For the solid phase membrane ELISA, 40 ul of 0.1 mg/ml breast cancer membrane protein were placed in polyvinyl chloride (PVC) microtiter wells for 12 hours at 4° C. The extract was aspirated and the wells washed with phosphate buffered saline (PBS) containing 1% bovine serum albumin (BSA). The wells were then incubated with 45 ul of a 1:10 dilution of hybridoma supernatant. The diluent was media with 25 mM of a buffer, 10% bovine serum, and 0.1% sodium azide. After 30 minutes at room temperature, the wells were again washed and incubated 45 minutes at 37° C. with a 1:200 dilution of peroxidase conjugated goat anti-mouse IgG. The diluent was PBS. The wells were then washed with PBS and reacted with 200 µl of 1,2-azino-di(3ethylbenzthiazoline sulphonic acid) in 0.1 M sodium citrate buffer pH 4.2 for 30 minutes at room temperature. Optical density was measured at 405 nm on a MicroElisa Reader. For each experiment a positive control, anti-beta 2 microglobulin at 5 µg/ml, was reacted with normal human kidney membrane. This gave an optical density of 1.0±0.1 (standard deviation). The background was 0 0.1 optical density units (O.D.) using media without mouse monoclonal antibody. Wells that gave a reaction on the breast cancer membrane extract of greater than O.D. were saved.

For the indirect immunofluorescence cell line assay 100,000 breast cancer cells of the imrunizing cell line were placed overnight with appropriate media in each chamber of a set of eight chambered slides. Similarly, 100,000 fibroblast cells from cell line CC95 were incubated overnight in chambered slide wells. The cells were washed with PBS containing 1% BSA. The wells, both breast cancer and fibroblast, were incubated for 30 minutes at 4° C. with 1:10 dilutions of hybridoma supernatant. The cells were again washed and incubated 30 minutes at 4° C. with a 1:50 dilution of fluorescein isothiocyanate (FITC)-conjugated goat F(ab')2 anti-mouse Ig. The cells were washed three times, fixed in 1.5% formaldehyde in PBS for five minutes, chambers removed and rinsed in PBS. The slides were then mounted in a composition containing polyvinyl alcohol, glycerol, buffers and a preservative and examined with a fluorescence microscope. Hybridoma wells showing strong fluorescent binding to the breast cancer cells but no fluorescent binding to fibroblasts were saved. Five thousand one hundred fifty-six hybridoma wells revealed breast cancer reactivity in the initial screen.

Supernatants from the 5156 positive wells were then tested in solid phase ELISA with seven normal tissue membrane extracts (liver, lung, colon, stomach, kidney, tonsil, and spleen). Any supernatant giving an ELISA O.D. greater than 0.3 was discarded. One thousand one hundred one of the supernatants were found to be unreactive with the normal tissue extracts.

The 1101 hybridoma supernatants were tested on frozen sections of human breast carcinoma tissues. Six micron sections were attached to slides, fixed 10 minutes in acetone at 4° C., dried 10 minutes at room temperature, washed with PBS, blocked with horse serum and incubated 20 minutes at room temperature with 100 ul neat hybridoma supernatant. The slides were washed with PBS, and finally incubated 20 minutes at 37° C. with a 1:50 dilution of peroxidase conjugated rabbit anti-mouse Ig, washed again with PBS, and finally incubated 7.5 minutes at 37° C. with 0.5 mg/ml diaminobenzidine in 0.05M Tris buffer pH 7.2 containing 0.01% hydrogen peroxide. The slides were stained with hematoxylin, dehydrated and mounted in a medium containing 35.9% methyl/n-butylmethacrylate copolymer, 7.1% butyl benzyl phthalate, and 0.3% 2,6-ditertbutyl-p-cresol. One hundred twenty-four wells yielded breast cancer selective binding and were cloned.

Purification and Class Determination

Imaunoglobulin class and subclass of the monoclonal breast cancer selective antibodies were determined by an immunodot assay essentially the same as that described in McDougal et al. *J. Immunol. Meth.* 63:281-290 (1983). Antibodies were also internally labeled by 9rowing $2-3\times10^6$ hybridoma cells for four hours in methionine-free medium containing 0.2 $\mu$Ci$^{35}$S methionine. $^{35}$S-labeled antibodies were immunoprecipitated with fixed staphylococcus A cells, or with fixed staphylococcus A cells precoated with rabbit anti-mouse immunoglobulin, and the immunoprecipitates were analyzed by SDS-PAGE to determine antibody light and heavy chain mobility, lack of extra chains, and the ability of each antibody to bind staphylococcal protein A.

The antibodies were expanded in vivo. Balb/c or FI (C57B/6 x Balb/c) mice were primed with 0.5 ml pristane intraperitoneally (ip) and after 10-14 days inoculated with one million log phase hybridoma cells in PBS. Ascites fluid was stored at −70° C. and thawed and filtered through a 0.8 micron filter unit before further purification.

Some IgG antibodies that bound staphylococcal protein A were purified by affinity chromatography on protein A-chromatographic resin containing either agarose, dextran and/or acrylamide with pH step gradient elution. IgG antibodies that did not bind protein A were precipitated by addition of ammonium sulfate to 40% saturation at 0° C.. or by binding to DEAE or Affigel TM (Biorad, Richmond, Calif.). Alternatively, IgG antibodies were purified by chromatography using a SephacrYl S-200 column, followed by DEAE cellulose as described. The precipitates were redissolved in PBS, dialysed to 20 rM Tris pH 7.2 and chromatographed on a 1.6×50 cm column of diethylaminoethyl cellulose (DEAE) eluting with a 1.5 liter 0-600 rM NaCl gradient at 4° C. at a flow rate of 1 ml/min. In each case, column fractions were monitored by SDS-PAGE and the purest antibody fractions were pooled, concentrated to 1-3 mg/ml, dialysed to PBS/0.02% NaN3, and stored at 4° C.

IgM antibodies were purified by gel filtration material on a 2.6×40 cm column of Sephacryl S-300 or other gel filtration or resin containing agarose, dextran and/or acrylamide, eluting with PBS/0.01% sodium azide at room temperature at a flow rate of 1 ml/min.

Selectivity Determination

In order to evaluate their selectivity, the purified antibodies were tested by immunoperoxidase section staining on sections of sixteen normal tissues, and by imaunofluorescent cell sorting on five blood cell types. Immunoperoxidase staining was performed as above except that known dilutions of purified antibodies in PBS in the range of 1-40 $\mu$g/ml were used instead of hybridoma supernatants. The pure antibodies were first titrated to find the minimal concentration giving strong immunoperoxidase staining on breast cancer sections and then used at the concentration for the normal tissue tests. No normal ovarian tissue showed detectable binding.

Peripheral blood cells (platelets, lymphocytes, red blood cells, granulocytes, and monocytes) were prepared by centrifugation using a medium which separates monocytes from polymorphonuclear leukocytes. The cells were reacted with antibody at the optimal concentration determined above for 30 minutes at 4° C., washed, reacted with a 1:50 dilution of fluorescein isothiocyanate-conjugated goat anti-mouse Ig for 30 minutes at 4° C., washed again and examined in a cell sorter. The wash buffer and diluents were PBS with 1% gelatin and 0.02% sodium azide. The cell sorter was equipped with a 76 micron nozzle and a one watt argon ion laser at 488 nm. An 80 mm confocal lens was used on the optical rail assembly for focusing. Other filters used were a 515 nm interference filter and a 515 nm absorbance filter (for scattered laser light) and a neutral density 1.5 filter for forward angle light scatter. Contour plots of log fluorescein fluorescence versus forward angle light scatter were used for sample analysis.

The binding behaviors on normal tissue sections of the antibodies useful in the imrunotoxins according to the invention are reported in Table 1 below. The following abbreviations are used to denote structures bound by the antibodies: Ac, acini; G, glands; T, tubules; D, ducts; L, lumen; W, sweat glands; E, epithelium; S, sebaceous glands; Gr, granulocytes; Mk, megakaryocytes; M, macrophage; Ly, lymphocytes; Bl, Basal layer; Fe, focal epithelium; A, aveolar lining cells; B, Bowman's capsule; Mu, muscle; I, islets; X, ganglia/nerve; V, blood vessel; and H, hair follicle. Selectivity was quantified as described hereinabove. The binding behavior of the antibodies on peripheral blood cells is reported in Table 2. The selectivity of the monoclonal antibodies is set out in Table 3.

TABLE 1

| NORMAL TISSUE BINDINGS OF OVARIAN MABS | | | | | | | | | |
|---|---|---|---|---|---|---|---|---|---|
| MAB | PANCREAS | ESOPHAGUS | LUNG | KIDNEY | COLON | STOMACH | BRAIN | TONSIL | LIVER |
| 1 2G3 | 2Ac | 2E | 1A | 2T | 0 | 1L | 0 | 1E | 0 |
| 2 9C6 | 0 | 2E | 0 | 0 | 0 | 1L | 0 | 1Ly,2E | 0 |
| 3 33F8 | 0 | 2E | 0 | 1T | 0 | 0 | 0 | 1Ly | 0 |
| 4 44B2 | 0 | 1E | 0 | 0 | 0 | 1G | 0 | 0 | 1 |
| 5 44F4 | 1Ac | 2E | 0 | 1T,B | 1L | 2L | 0 | 1E | 0 |
| 6 120H7 | 0 | 1E | 0 | 1T | 0 | 1L | 0 | 0 | 0 |
| 7 200F9 | 1Ac | 0 | 0 | 2L | 0 | 0 | 0 | 0 | 0 |
| 8 204F4 | 0 | 2E | 0 | 2T | 2X | 2X | 0 | 2Ly,E | 0 |

TABLE 1-continued
NORMAL TISSUE BINDINGS OF OVARIAN MABS

| | | | | | | | | | | |
|---|---|---|---|---|---|---|---|---|---|---|
| 9 219F3 | 1Ac | 2E | 0 | 1T | 0 | 0 | 0 | 1Ly,E | 0 | |
| 10 245E7 | 1L | 0 | 1A,M | 0 | 0 | 2L | 0 | 1E | 0 | |
| 11 260F9 | 1Ac | 2E | 0 | 1T | 0 | 1G | 0 | 2E | 2D | |
| 12 266B2 | 1Ac,1D | 2E | 0 | 1T | 0 | 0 | 0 | 2E | 0 | |
| 13 280D11 | 0 | 1E | 0 | 2T,B | 1L | 2L | 0 | 0 | 2D | |
| 14 317G5 | 1Ac,I | 0 | 0 | 2T | 1G | 0 | 0 | 0 | 2D | |
| 15 369F10 | 0 | 0 | 0 | 0 | 0 | 1G | 0 | 0 | 0 | |
| 16 388D4 | 2Ac,1I | 2E | 0 | 1-2T | 1-2G | 1L | 0 | 1E | 0 | |
| 17 421E8 | 1Ac | 1E | 0 | 1T | 0 | 1G | 0 | 0 | 1 | |
| 18 451C3 | 0 | 0 | 2M | 0 | 0 | 0 | 1V | 2Ly,1BL | 0 | |
| 19 454A12 | 0 | 0 | 1M | 0 | 1G | 0 | 0 | 0 | 0 | |
| 20 454C11 | 1D | 1-2E | 0 | 1T | 0 | 1G | 0 | 1E | 1D | |
| 21 650E2 | 1Ac,I | 0 | 1-2A | 2T | 2G | 0 | 0 | 0 | 2D | |
| 22 788G6 | 0 | 0 | 0 | 2T | 0 | 0 | 0 | 1FE | 0 | |
| 23 871E3 | 2I,Ac,D | 1FE | 0 | 0 | 1G | 1G,2Gr | 0 | 1E,Ly | 0 | |

| MAB | HEART | OVARY | SKIN | BONE MARROW | UTERUS | BLADDER | NORMAL BREAST |
|---|---|---|---|---|---|---|---|
| 1 2G3 | 0 | 0 | 0 | 0 | 2L | 2E | 2E |
| 2 9C6 | 0 | 0 | 0 | 2Gr | 0 | 0 | 2E |
| 3 33F8 | 0 | 0 | 1W | 1Mk | 1L | 1E | 0 |
| 4 44B2 | 0 | 0 | 0 | 0 | 0 | 0 | 0 |
| 5 44F4 | 0 | 0 | 1H | 2Gr | 2L | 0 | 2E |
| 6 120H7 | 0 | 0 | 2S | 0 | 2L | 0 | 0 |
| 7 200F9 | 0 | 0 | 2S | 0 | 0 | 0 | 0 |
| 8 204F4 | 0 | 0 | 2S,W | 0 | 2L | 0 | 1E |
| 9 219F3 | 0 | 0 | 2H,W | 1-2Gr | 1G | 0 | 2E |
| 10 245E7 | 0 | 0 | 2S | 0 | 2L | 1E | 2L |
| 11 260F9 | 0 | 0 | 2E,2H | 0 | 1L | 2E | 2E |
| 12 266B2 | 0 | 0 | 2E,2W | 0 | 0 | 1E | 1E |
| 13 280D11 | 0 | 0 | 1E,1H | 2Gr | 2G | 0 | 2L |
| 14 317G5 | 0 | 0 | 0 | 0 | 1G | 0 | 0 |
| 15 369F10 | 0 | 0 | 1S | 0 | 0 | 0 | 0 |
| 16 388D4 | 0 | 0 | 2E,S,W | 0 | 1G | 2E | 1 |
| 17 421E8 | 0 | 0 | 0 | 0 | 1G | 0 | 0 |
| 18 451C3 | 0 | 0 | 0 | 2 | 1G | 0 | 0 |
| 19 454A12 | 0 | 0 | 0 | 1 | 1E | 0 | 0 |
| 20 454C11 | 0 | 0 | 1E,H | 0 | 1G | 1E | 1E |
| 21 650E2 | 0 | 0 | 0 | 0 | 2G | 0 | 1 |
| 22 788G6 | 0 | 0 | 0 | 0 | 0 | 0 | 0 |
| 23 871E3 | 0 | 2Gr | 1S | 0 | 0 | 0 | 0 |

TABLE 2
BLOOD CELL BINDING OF OVARIAN MABS

| MAB | RBC | PLATELET | LYMPHOCYTE | GRANULOCYTE | MONOCYTE |
|---|---|---|---|---|---|
| 1 2G3 | 0 | 0 | 0 | 0 | 0 |
| 2 9C6 | 0 | 0 | 0 | 0 | 0 |
| 3 33F8 | 0 | 0 | 0 | 0 | 0 |
| 4 44B2 | 0 | 0 | 0 | 0 | 0 |
| 5 44F4 | 0 | 0 | 0 | 2 | 0 |
| 6 120H7 | 0 | 0 | 0 | 0 | 0 |
| 7 200F9 | 0 | 0 | 0 | 0 | 0 |
| 8 204F4 | 0 | 0 | 0 | 0 | 1 |
| 9 219F3 | 0 | 0 | 0 | 0 | 0 |
| 10 245E7 | 0 | 0 | 0 | 0 | 0 |
| 11 260F9 | 0 | 0 | 0 | 0 | 0 |
| 12 266B2 | 0 | 0 | 0 | 0 | 0 |
| 13 280D11 | 0 | 0 | 0 | 2 | 0 |
| 14 317G5 | 0 | 0 | 0 | 0 | 0 |
| 15 369F10 | 0 | 0 | 0 | 0 | 0 |
| 16 388D4 | 0 | 0 | 0 | 0 | 0 |
| 17 421E8 | 0 | 0 | 0 | 0 | 0 |
| 18 451C3 | 0 | 0 | 0 | 0 | 0 |
| 19 454A12 | 0 | 0 | 0 | 0 | 0 |
| 20 454C11 | 0 | 0 | 0 | 0 | 0 |
| 21 650E2 | 0 | 0 | 0 | 0 | 0 |
| 22 788G6 | 0 | 0 | 0 | 0 | 0 |
| 23 871E3 | 0 | 0 | 0 | 0 | 0 |

TABLE 3
TISSUE SELECTIVITY OF OVARIAN MABS

| MAB | BLOOD CELLS BOUND | NORMAL TISSUE SUBSTRUCTURES BOUND/NORMAL TISSUE SUB-STRUCTURES AND BLOOD CELLS | SELECTIVITY |
|---|---|---|---|
| 1 2G3 | 0/5 | 9/128 | 0.070 |
| 2 9C6 | 0/5 | 6/128 | 0.047 |
| 3 33F8 | 0/5 | 7/128 | 0.055 |
| 4 44B2 | 0/5 | 3/128 | 0.023 |
| 5 44F4 | 1/5 | 12/128 | 0.094 |
| 6 120H7 | 0/5 | 5/128 | 0.039 |
| 7 200F9 | 0/5 | 3/128 | 0.023 |
| 8 204F4 | 1/5 | 11/128 | 0.086 |
| 9 219F3 | 0/5 | 10/128 | 0.078 |
| 10 245E7 | 0/5 | 9/128 | 0.070 |
| 11 260F9 | 0/5 | 11/128 | 0.086 |
| 12 266B2 | 0/5 | 9/128 | 0.070 |
| 13 280D11 | 1/5 | 12/128 | 0.094 |
| 14 317G5 | 0/5 | 6/128 | 0.047 |
| 15 369F10 | 0/5 | 2/128 | 0.016 |
| 16 388D4 | 0/5 | 13/128 | 0.102 |
| 17 421E8 | 0/5 | 6/128 | 0.047 |
| 18 451C3 | 0/5 | 6/128 | 0.047 |
| 19 454A12 | 0/5 | 4/128 | 0.031 |
| 20 454C11 | 0/5 | 10/128 | 0.078 |
| 21 650E2 | 0/5 | 8/128 | 0.063 |
| 22 788G6 | 0/5 | 2/128 | 0.016 |
| 23 871E3 | 0/5 | 11/128 | 0.086 |

Cancer Tumor Binding of Anti-Ovarian Cancer Monoclonal Antibodies

The antibodies were tested by immunoperoxidase staining on eleven non-breast malignancies. The results of the antibodies are reported in Table 4 below.

TABLE 4

| | NONBREAST CANCER BINDINGS OF OVARIAN MABS | | | | | | | | | | |
|---|---|---|---|---|---|---|---|---|---|---|---|
| MAB | COLON | LUNG | PRO-STATE | PAN-CREAS | UTERUS | LYM-PHOMA | STO-MACH | BLADDER | ESO-PHAGUS | MELA-NOMA | OVA-RIAN |
| 1 2G3 | 2 | 0 | 2 | 0 | 2 | 0 | 2 | 0 | 0 | 0 | 2 |
| 2 9C6 | 1 | 0 | 0 | 0 | 2 | 1 | 0 | 0 | 0 | 0 | 1 |
| 3 33F8 | 0 | 1 | 0 | 0 | 1 | 0 | 0 | 0 | 0 | 0 | 1 |
| 4 44B2 | 0 | 0 | 0 | 0 | 0 | 0 | 0 | 1 | 0 | 0 | 1 |
| 5 44F4 | 1 | 0 | 1 | 0 | 1 | 0 | 0 | 0 | 0 | 0 | 2 |
| 6 120H7 | 0 | 0 | 2 | 0 | 1 | 1 | 0 | 0 | 0 | 0 | 2 |
| 7 200F9 | 0 | 1 | 0 | 0 | 0 | 0 | 0 | 0 | 0 | 0 | 1 |
| 8 204F4 | 0 | 1 | 2 | 1 | 2 | 1 | 0 | 0 | 0 | 0 | 2 |
| 9 219F3 | 0 | 0 | 1 | 0 | 1 | 1 | 0 | 0 | 0 | 0 | 1 |
| 10 245E7 | 0 | 2 | 2 | 2 | 2 | 2 | 0 | 0 | 0 | 0 | 2 |
| 11 260F9 | 0 | 0 | 1 | 1 | 1 | 0 | 0 | 0 | 1 | 0 | 2 |
| 12 266B2 | 0 | 1 | 1 | 1 | 1 | 0 | 1 | 0 | 1 | 0 | 1 |
| 13 280D11 | 0 | 0 | 1 | 1 | 1 | 2 | 0 | 0 | 0 | 0 | 2 |
| 14 317G5 | 1 | 1 | 0 | 0 | 1 | 0 | 0 | 0 | 0 | 0 | 1 |
| 15 369F10 | 0 | 1 | 1 | 1 | 0 | 0 | 0 | 0 | 0 | 0 | 2 |
| 16 388D4 | 1 | 1 | 2 | 1 | 2 | 0 | 0 | 0 | 1 | 1 | 1 |
| 17 421E8 | 1 | 1 | 1 | 1 | 1 | 0 | 0 | 0 | 1 | 0 | 1 |
| 18 451C3 | 1 | 1 | 1 | 1 | 2 | 1 | 2 | 1 | 2 | 1 | 1 |
| 19 454A12 | 0 | 0 | 0 | 1 | 2 | 0 | 1 | 1 | 2 | 2 | 1 |
| 20 454C11 | 0 | 0 | 1 | 1 | 2 | 0 | 0 | 0 | 0 | 0 | 1 |
| 21 650E2 | 2 | 2 | 2 | 2 | 2 | 0 | 0 | 0 | 0 | 0 | 2 |
| 22 788G6 | 0 | 2 | 0 | 0 | 0 | 0 | 0 | 0 | 0 | 0 | 2 |
| 23 871E3 | 0 | 2 | 0 | 1 | 0 | 0 | 0 | 0 | 0 | 0 | 1 |

Antibody Affinity and Antigen Density

Several of the antibodies were iodinated and tested for binding to MCF-7, CAMA1, SKBR3 or ZR7530 cells. The antibodies were labeled with $^{125}$I using chloramine T or Iodogen TM to a specific activity of approximately 5-10 $\mu$Ci/$\mu$g. To determine immunoradiochemical purity, 100,000 cpm of two of the labeled antibodies in 0.5 ml fetal calf serum was serially absorbed with five aliquots of target cells for 15 minutes at 0° C. (generally 4,000,000 cells per aliquot), and the remaining radioactivity in the supernatant after each absorption was determined.

For measurements of association constants, known concentrations of labeled and unlabeled monoclonal antibodies were incubated with target cells in fetal calf serum for 15 minutes on ice. Aliquots of the cell/antibody mix were then counted in a gamma counter or filtered through Microfold filter plates (V & P Scientific) and the filters counted. To account for unbound antibody retained in liquid on the filters, controls containing the same concentrations of antibody but no cells were done in parallel. Association constants and antigen copy number per target are calculated from the affinity test results and are reported in Table 5 below.

TABLE 5

| AFFINITY AND ANTIGEN COPY NUMBER OF OVARIAN MABS | | | |
|---|---|---|---|
| MAB | n | Ka | CELL LINE |
| 1 2G3 | 3700000 | $9.1 \times 10^6$ | MCF7 |
| 2 9C6 | | | |
| 3 33F8 | | | |
| 4 44B2 | | | |
| 5 44F4 | 2100000 | $5.3 \times 10^6$ | MCF7 |
| 6 120H7 | 210000 | $2 \times 10^7$ | MCF7 |
| 7 200F9 | | | |
| 8 204F4 | 3200000 | $8.0 \times 10^6$ | MCF7 |
| 9 219F3 | | | |
| 10 245E7 | | | |
| 11 260F9 | 310000 | $5.6 \times 10^7$ | MCF7 |
| 12 266B2 | 80000 | $2.7 \times 10^8$ | MCF7 |
| 13 280D11 | 390000 | $8.8 \times 10^6$ | MCF7 |
| 14 317G5 | 3200000 | $1.6 \times 10^6$ | CAMA1 |
| 15 369F10 | | | |
| 16 388D4 | | | |
| 17 421E8 | | | |
| 18 451C3 | 400000 | $4 \times 10^8$ | MCF7 |
| 19 454A12 | 470000 | $1.2 \times 10^8$ | MCF7 |
| 20 454C11 | 390000 | $4.8 \times 10^7$ | ZR7530 |
| 21 650E2 | | | |
| 22 788G6 | | | |
| 23 871E3 | | | |

Characterization of Antigen Specificty

In order to identify the antigens recognized by the monoclonal antibodies, immunoprecipitation of the antigens was carried out according to the following method. Eight mm diameter polystyrene balls (Precision Plastic Ball Co.) were covered with 10% fuming nitric acid in glacial acetic acid and were incubated for three hours in a 50° C. water bath. Following the acid treatment, the balls were rinsed three times with distilled water, covered with 1% sodium dithionite in 0.1M NaOH and incubated three hours in a 50°0 C. water bath. The balls were again rinsed three times with distilled water, covered with 0.1% 1-ethyl-3-(3-dimethylaminopropyl)-carbodiimide (EDAC), 0.2% suberic acid (suberic acid dissolved in dimethylformamide) and incubated overnight at room temperature. The balls were rinsed three times with distilled water, and marked for identification.

Purified monoclonal antibodies were diluted 0.2 mg/ml in 2-(N-morpholino)ethane sulfonic acid buffer, and the previously treated and marked polystyrene balls were placed in individual tubes and covered with 450 microliters diluted antibody and 50 microliters of fresh 1% EDAC. Tubes were capped and incubated at 25° C. for 24 hours. Following this incubation, the balls were rinsed twice with PBS and were either used fresh or were stored for several days at 4° C. before use.

Freshly labeled target cell extracts were prepared from human breast cancer cell lines labeled with 125-I by the lactoperoxidase method of Marchalonis, J., "An Enzymic Method for the Trace Iodination of Imaunoglobulins and other Proteins', *Biochem. J*113:299–305 (1969), or with 35-S by growth in 35-S methionine. The labeled cells were dissolved in solubilization buffer (1% (v/v) Triton X-100, 150 rM NaCl, 5 mM EDTA, 25 mM Tris-HCl, pH 7.5). Four parts of labeled extract were mixed in a vessel with one part solubilization buffer containing 50 mg/ml bovine serum albumin, to give a final concentration of 10 mg/ml BSA. The balls coated with monoclonal antibody were added to the vessel and were incubated four hours on ice with shaking. Labeled antigen was pipetted from the vessel and the balls were rinsed four times with solubilization buffer. The balls were then removed, placed in individual tubes with 100 microliter Laemmli SDS gel sample buffer, and were incubated three minutes in boiling water. The balls were removed and the samples were run on an SDS gel with appropriate standards.

Imaunoprecipitation tests on the antibodies indicated that eight of them (2G3, 120H7, 200F9, 204F4, 245E7, 369F10, 788G6, and 871E3) all bind to high molecular weight mucins (HMW). Two (260F9 and 266B2) bind to the same epitope of a 55 Kd glycoprotein antigen. Two (317G5 and 650E2) bind to a 42 Kd antigen. Two antibodies (451C3 and 454A12) bound to transferrin receptors in the form of a 95 Kd antigen. Neither 451C3 nor 454A12 blocked binding of transferrin to the receptor. The antigen binding characteristics of the monoclonal antibodies that were tested are summarized in Table 6.

TABLE 6
ANTIGENS RECOGNIZED BY OVARIAN MONOCLONAL ANTIBODIES

| MAB | ANTIGEN |
|---|---|
| 1 2G3 | HMW |
| 2 9C6 | 75 Kd |
| 3 33F8 | 66 Kd |
| 4 44B2 | |
| 5 44F4 | 18, 39, 72, 81, 175 Kd (all diffuse bands) |
| 6 120H7 | HMW |
| 7 200F9 | HMW |
| 8 204F4 | HMW |
| 9 219F3 | |
| 10 245E7 | HMW |
| 11 260F9 | 55 Kd |
| 12 266B2 | 55 Kd |
| 13 280D11 | |
| 14 317G5 | 42 Kd |
| 15 369F10 | HMW |
| 16 388D4 | |
| 17 421E8 | |
| 18 451C3 | 95 Kd (TRANSFERRIN RECEPTOR) |
| 19 454A12 | 95 Kd (TRANSFERRIN RECEPTOR) |
| 20 454C11 | 200 Kd |
| 21 650E2 | 42 Kd |
| 22 788G6 | HMW |
| 23 871E3 | HMW |

Antibody Isotype

Antibody isotype was determined as follows: A grid of 5-mm squares is lightly drawn in pencil on the nitrocellulose sheet and 1-ml droplets of antiisotype sera (Litton Bionetics, Kensington, Md., rabbit antisera to mouse κ, λ, α,γ1, γ2a, γ2b, γ3, and μ chains) are applied so that each row of squares receives one spot of each heavy and light chain reagent. The sheet is incubated one hour at room temperature in a moist chamber, rinsed quickly in PBS-BSA, containing 1% (w/v), and left overnight in PBS-BSA at 4° C. Strips are cut apart with a scissors and may be stored at 4° C. in PBS-BSA containing 0.02% sodium azide. Alternatively, strips may be air-dried and stored desiccated at 4° C. A series of small tubes is prepared containing 3 ml hybridoma culture supernatant or supernatant diluted with PBS-BSA. 1:10 dilutions are generally successful; and some supernatants can be diluted as much as 1:200. A nitrocellulose strip is incubated in each tube for one hour at room temperature. The strips are rinsed three times in PBS-BSA and incubated for one hour at room temperature in diluted rabbit anti-mouse-horseradish peroxidase. The strips are rinsed twice in PBS-BSA and twice in Tris buffer. The strips are placed in Tris buffer containing diaminobenzidine and hydrogen peroxide until sufficient color develops on the anti-isotype spots (usually 3–4 minutes). The antibody isotypes are indicated in Table 7.

TABLE 7
ISOTYPE OF OVARIAN MONOCLONAL ANTIBODIES

| MAB | ISOTYPE |
|---|---|
| 1 2G3 | G1 |
| 2 9C6 | M |
| 3 33F8 | G1 |
| 4 44B2 | G1 |
| 5 44F4 | G3 |
| 6 120H7 | M |
| 7 200F9 | G1 |
| 8 204F4 | M |
| 9 219F3 | G1 |
| 10 245E7 | G1 |
| 11 260F9 | G1 |
| 12 266B2 | G1 |
| 13 280D11 | G1 |
| 14 317G5 | G1 |
| 15 369F10 | M |
| 16 388D4 | G1 |
| 17 421E8 | G1 |
| 18 451C3 | G1 |
| 19 454A12 | G1 |
| 20 454C11 | G2A |
| 21 650E2 | G1 |
| 22 788G6 | G1 |
| 23 871E3 | M |

Cytotoxicity Evaluation

The antibodies were treated with SPDP as described by Bjorn et al., "Evaluation of Monoclonal Antibodies for the Development of Breast Cancer Immunotoxins," *Cancer Res.*45:1214–1221 (1985) and Carlsson, J. et al., *Biochem. J.* (1978) 173:723–737 or with iminothiolane (IT) and were conjugated to ricin toxin A chain (RTA) to make the claimed immunotoxins.

SPDP Conjugation of RTA to the Monoclonal Antibodies

SPDP (20 aM in ethanol) was added in a 20-fold molar excess to antibody and following a 30 min incubation at room temperature, the unreacted SPDP was removed by dialysis against PBS. The extent of derivatization was determined by measuring the release of pyridine-2-thione at 343 nm after reduction with dithiothreitol (DTT). Depending on the antibody, three to eight lysine amino acid groups (per antibody molecule) were converted to the pyridyl-disulfide derivative.

The SPDP-treated antibodies were conjugated with RTA. Immediately prior to conjugation, the RTA was reduced with 50 mM DTT, then desalted on a column of chromatographic resin containing agarose, dextran and/or acrylamide to remove DTT from protein. Reduced RTA was added in a three- to five-fold molar excess over pyridyl-disulfide antibody. A typical reaction mixture (1 ml) consisted of 7 μM antibody and 30 um RTA. The reaction was allowed to proceed overnight at 4° C. The extent of conjugation of RTA to antibody was determined spectrophotometrically by measuring the release of pyridine-2-thione. On the average, conjugates contained two to three RTA molecules per antibody molecule. This was confirmed by nonreducing L. SDS-PAGE gels (7.5%), which also revealed that the typical conjugate Preparation contained 10%-30% free antibody.

The conjugate mixture was chromatographed on a HPLC size exclusion column to separate conjugates from residual unreacted RTA. The column was equilibrated in 0.1 sodium sulfate/0.02 M sodium phosphte pH 6.8. Conjugate mixture (0.7 ml) was injected, then chromatographed at a flow rate of 1 ml/min (room teaperature). Fractions of 0.5 ml were collected and the peak conjugate fractions were pooled and filter sterilized prior to cytotoxicity testing.

Iminothiolane Conjugation of RTA to the Monoclonal

Approximately 30 mg/ml antibody in 0.10 M Na phosphate, 0.001 M Na EDTA, pH 8.0 (hereafter referred to as P-EDTA buffer) is reacted with 1 mM 5,5'-dithiobis-(2-nitrobenzoic acid) (DTNB) at room temperature for about 15 min and then chilled to 0° C. in an ice bath. Enough IT is added to this solution to give an average of 2.5 IT molecules/antibody molecule, and the resulting solution is dialysed at 0°-5° C. against three 100-fold excess volumes of P-EDTA buffer.

RTA, normally stored in P-EDTA containing 1 mM DTT, is ultrafiltered to a concentration between 10 and 15 mg/ml and dialyzed at 0°-5° C. against three 100-fold excess volumes of P-EDTA. Enough RTA is added to the derivatized antibody to give an average of 1.0-1.2 free thiols on RTA per blocked thiol on derivatized antibody. This mixture is incubated at room temperature for 2 hrs.

The coupling reaction mixture is applied to a column of a chromatographic resin based on a blue dye (trysacryl blue) covalently coupled to a solid support, which mixture is then eluted with P-EDTA at room temperature. The column is scaled to contain approximately 2 ml of bed volume per mg of starting antibody. After an initial peak of unconjugated antibody has been eluted from the column, the elutant is switched to P-EDTA containing 1 M NaCl. Imaunoconjugate and unreacted RTA are eluted in this buffer as a very. sharp peak, which is pooled and dialyzed at 0°-5° C. against one 10-fold excess volume of 0.15 M Na phosphate, pH 7.1 (hereafter referred to as pi buffer). The dialyzed protein is applied to a column of a size-exclusion gel at 0-5° C. and eluted with buffer at a flow rate of 6 cm/hr. The column is scaled to contain at least 25 ml of bed volume/ml of applied protein. Immunoconjugate is eluted as a single peak, slightly after the excluded volume, baseline-resolved from following peaks of dimerized and monomeric RTA. The pooled imnunoconjugate peak is ultrafiltered at 35 psi to a final concentration of 5.0 mg/ml and filter-sterilized.

The invention will be better understood in light of the following examples which are intended by the inventor to be merely exemplary and non-limiting.

EXAMPLE I

Female athymic nude mice (Nu/Nu, strain Balb/C), weighing between 16 and 22 grams were used. NIH-:OVCAR-3 ascites cells were obtained from carrier mice. The cells were washed twice in phosphate buffered saline (PBS) and resuspended in PBS at approximately 1 volume of cells to 2 volumes of PBS. Cell count was determined by counting in a haemocytometer. Cell viability was determined by trypan blue dye exclusion. Each animal was injected intraperitoneally with $5 \times 10^7$ viable cells on day zero. Animals were injected with the immunotoxins on days 4, 7 and 10. The imaunotoxin was usually admistered in 0.1ml PBS. Control animals were injected with 0.1ml PBS on the same schedule. Five animals were used for each dose of each immunotoxin tested and for the controls. Animals were observed daily. Effectiveness was determined by an increase in survival time relative to controls in each experiment or by less abdominal swelling due to retardation of the increase in tumor burden in treated animals as compared to controls having the same survival time.

The results are reported in Table 8. In Table 8, and the following tables, "Swelling Index' is defined as follows: 0 =no abdominal distension; 1=barely visible abdominal distension; 2 =moderate abdominal distension; and 3=severe abdominal distension:

TABLE 8

| Test Material | Dose | # Surviving | Swelling Index | Mean Life Span |
|---|---|---|---|---|
| | | Experiment A | | |
| 317G5-IT-RTA | 50 ug | 0 | — | 49.8 +/− 10 |
| | 100 ug | 2 | 3 | 60.2 +/− 5.2 |
| 260F9-IT-RTA | 50 ug | 0 | — | 26 +/− 1.4 |
| | 100 ug | 0 | — | 24.6 +/− 3.3 |
| 113F1-IT-RTA | 25 ug | 0 | 3 | 32.2 +/− 13.9 |
| | 50 ug | 0 | — | 29 +/− 3.0 |
| PBS Controls | 0.1 ml | 0 | — | 29 |

| Material | Dose | # Surviving (day 85) | Swelling Index | Mean Survival |
|---|---|---|---|---|
| | | Experiment B | | |
| PBS | — | 0 | 3 | 48 |
| 454A12-IT-rRTA | 25 ug | 1 | 2 | >74 |
| 280D11-IT-RTA | 50 ug | 1 | 2 | >66 |
| | 100 ug | 2 | 2 | >71 |
| 2G3-IT-RTA | 50 ug | 0 | 3 | 30 |

TABLE 8-continued

| | 100 ug | 0 | 3 | 35 |
|---|---|---|---|---|

EXAMPLE II

In the following example the experiment was run essentially as described in the previous example except that the animals were injected on days 4, 6 and 8. This example shows that the anti-tumor effect of immunotoxin 454A12-IT-rRTA is blocked when tumor bearing animals are treated with an excess of the monoclonal antibody 454A12 from which the immunotoxin is derived. MOPC21, an antibody which is not human ovarian tumor specific, when administered at excess with 454A12-IT-rRTA has no corresponding blocking effect.

TABLE 9

| Material | Dose (ug) # | # Surviving (day 69) | Swelling Index | Survival (mean days) |
|---|---|---|---|---|
| PBS | — | 0 | 3 | 41 |
| 454A12-IT-RTA | 25 | 4 | 0 | >69 |
| 454A12-IT-RTA + 454A12 (500 ug) | 25 | 0 | 3 | 26 |
| 454A12-IT-RTA + MOPC21 (500 ug) | 25 | 3 | 1 | >65 |
| 317G5-IT-RTA | 50 | 2 | 0 | >60 |
| | 100 | 4 | 0 | >65 |

EXAMPLE III

The procedure used in this experiment is essentially the same as Example I. This experiment shows that immunotoxins comprised of the Fab'2 fragment of 454A12 conjugated to RTA has antitumor activity comparable to 454A12-IT-RTA.

TABLE 10

| Material | Dose (ug) # | # Surviving (day 34) | Swelling | Survival (mean days) |
|---|---|---|---|---|
| PBS | — | 3 | 3 | >34 |
| 454A12-IT-RTA | 10 | 2 | 0 | >34 |
| 454A12-IT-RTA | 25 | 3 | 0 | >39 |
| 454A12-IT-RTA | 50 | 4 | 0 | >39 |
| 454A12-RTA (Fab'2) | 10 | 3 | 0 | >39 |
| | 25 | 4 | 0 | >39 |
| | 50 | 3 | 0 | >34 |

EXAMPLE IV

The following Example shows the in vitro cytotoxicity of the Immunoconjugates against several ovarian cancer cell lines.

Cell culture

NIH:OVCAR-2, -3, -4, and -5 are isolated from the malignant ascites of patients with ovarian carcinoma. These cell lines have been previously described in the following references which are herein incorporated by reference. Hamilton et al., "Characterization of Human Ovarian Carcinoma Cell Lines (NIH:OVCAR-3) with Androgen and Estrogen Receptors' *Cancer Res* 43:5379–5389 (1983). Hamilton et al., "Experimental Model Systems of Ovarian Cancer: Aplications to the Design and Evaluation of New Treatment Approaches' *Seminars in Oncology* 11:285–298 (1985). The ovarian cancer cell line A1847 was obtained from S. Aaronson (National Cancer Institute, Bethesda, Md.). The ovarian cells were grown in RPMI medium 1640, 10% fetal bovine serum, 10 ug/ml insulin and penicillin-streptomycin. KB cells were grown in Dulbecco's Modified Eagle Medium (DMEM), 10% calf serum, glutamine and penicillin-streptomycin. Tissue culture media, sera, glutamine and antibiotics were purchased from Grand Island Biological Col, Grand Island, N.Y., and insulin was obtained from Elanco Products Company, Indianapolis, Ind. For protein synthesis inhibition assays, cells were plated at $2 \times 10^5$ cells/35-mm dish one day prior to use. Before adding immunotoxins, cells were washed twice with DMEM containing bovine serum albumin (2 mg/ml) (DMEM-BSA). The listed immunotoxins were made by iminothiolane derivitization and conjugation to RTA as described hereinabove.

Protein Synthesis Assay

Inhibition of protein synthesis was used to measure the activity of the immunotoxins. Cells were incubated with DMEM-BSA containing various concentations of immunotoxins at 37° C. for 24 h and then assayed for incorporation of [$^3$H]leucine (New England Nuclear, Boston, Mass., specific activity 140.8 Ci/mmol) into TCA-insoluble material as described in Pirker et al. "Anti-Transferrin Receptor Antibody Linked to *Pseudomonas* Exotoxin: A Model Immunotoxin in Human Ovarian Carcinoma Cell Lines' *Cancer* 45:751–757 (1985). Mean values of duplicates were expressed as a percentage of controls of the same cell line which did not receive immunotoxins. Immunoconjugates that gave 50% inhibition of protein synthesis as compared to untreated controls (ID50) of 10nM or less were considered to be effective. $ID_{50}$ of the immunoconjugates tested are listed below in Table 11.

TABLE 11

| | IN VITRO CYTOTOXICITY $ID_{50}$(nM) | | | | | |
|---|---|---|---|---|---|---|
| RTA CONJUGATE | OV-2 | OV-3 | OV-4 | OV-5 | A1847 | KB |
| 454A12 | 0.04 | 0.05 | 0.05 | 0.03 | — | 0.01 |
| 317G5 | 0.1 | 0.2 | 0.1 | 0.3 | — | 0.1–2 |
| 260F9 | 0.2 | 0.5 | 0.2 | 0.2 | >5 | 140 |
| 113F1 | — | 2 | — | — | — | — |
| 280I1 | >30 | 4 | 13 | >20 | >30 | 120 |
| 2G3 | — | 8 | — | — | — | — |
| 369F10 | — | 10 | — | — | — | — |
| 454C11 | >5 | >5 | >5 | >5 | >5 | >5 |
| 520C9 | >5 | — | — | — | — | — |
| 245E7 | >30 | >30 | >30 | 30 | >30 | >30 |

EXAMPLE V

The immunoconjugates described in the immediately preceeding example were tested against NIH:OVCAR-3 cells. Cells were maintained in RPM1 medium 1640, 10% fetal bovine serum, 10 μg/ml insulin and penicillin-streptomycin. Cells were removed from the culture flasks by mild trypsin digestion or versene addition. The cell concentration was adjusted. $4 \times 10^5$ NIH OVCAR-3 cells were suspended in 1 ml of medium and were added to 8-ml glass vials (ICN), followed by the addition of conjugate dilutions (in PBS containing bovine serum albumin, 100 μg/ml). After incubation at 37o for 22 hrs., the medium was aspirated, the monolayers were washed with PBS, and 0.5 ml methionine-free medium supplemented with 0.5 μCi L-[$^5$S]methionine (Amersham; 1400 Ci/mmol) was added. After a 2-hr incubation at 37°, the medium was aspirated, and the cell monolayers were washed twice with 10% trichloroacetic acid containing methionine (1 mg/ml). The cells were dried, scintillation fluid was added, and the radioactivity was measured in a Packard CL/D liquid scintillation counter.

Inhibition of protein synthesis was calculated as the incorporation of TCA precipitable $^{35}$S counts for each vial. Mean values were expressed as a percentage of controls of the same cell line that did not receive immunotoxins. $ID_{50}$s were determined as in the immediately preceeding example. The results are reported in the following Table 12.

TABLE 12

| In Vitro Cytotoxicity vs. OVCAR-3 | |
|---|---|
| CONJUGATE | $ID_{50}$(nM) |
| 454A12-RTA | 0.05 |
| 454A12-RTA | 0.2 |
| 454A12-(Fab')$_2$-RTA | 0.4 |
| 317G5-RTA | 0.2 |
| 113F1-RTA | 2 |
| 2G3-RTA | 3 |
| 260F9-RTA | 4 |
| 280D11-RTA | 30 |
| 454C11-RTA | 50 |
| 369F10-RTA | >56 |
| 245E7-RTA | >56 |
| 520C9-RTA | >112 |
| MOPC21-RTA | >112 |
| MOPC21-RTA | >80 |

EXAMPLE VI

This Example shows the cytotoxicity of immunoconjugates prising the monoclonal antibodies described above and Pseudomonas exotoxin.

Pseudomonas exotoxin (PE) was a gift of Dr. S. Leppla (Ft. Detrick, Frederick, Md.). PE may also be obtained commercially from Swiss Serum and Vaccine Institute, Berne, Switzerland. PE conjugates were constructed and purified by a modification of a method previously incorporated herein by reference. Pirker et al. (1985). PE (30 nmol) was reacted with 5000 nmol 2-iminothiolane-HCI (Pierce Chemical Co., Rockford, Ill.) and 500 nmol NAD+ in 1 ml 0.1 M phosphate buffer (pH 8.0) containing 1 mM EGTA at 37° C. for 1 h. The derivatized PE was then separated from the reactants using HPLC and activated by the addition of 5,5'-dithio-bis(2-nitrobenzoic acid) (DTNB) to a final concentration of 1 mM. Antibodies (40–50 nmol) were incubated with 100–200 nmol 2-iminothiolane-HCl in 0.75 ml 0.1 M phosphate buffer (pH 8.0) containing 1 mM EGTA at 37° C. for 1 h. The antibodies were reacted with the activated PE and the conjugates were purified using HPLC as described. Pirker et al. (1985). A peak containing a one-toone conjugate of PE with the antibody was recovered and used for all studies described below.

Inhibition of protein synthesis and $ID_{50}$'s were determined as described above in Example IV except that the cells were incubated with immunotoxin for 12 hrs. Results from representative protein inhibition assays are shown and the average $ID_{50}$ values of all experiments are provided in Table 13. $ID_{50}$'s are shown as ng/ml and (nM) in the table.

TABLE 13

| | $ID_{50}$-Values in ng/ml (nM) for Protein Synthesis Inhibition[a] | | |
|---|---|---|---|
| Cells | 454C11-PE | 260F9-PE | 280D11-PE |
| OVCAR-2 | 1.6 (0.01) | 3.4 (0.02) | 835 (4) |
| OVCAR-3 | 3.6 (0.02) | 41.5 (0.2) | 805 (4) |
| OVCAR-4 | 0.7 (0.005) | 4.7 (0.02) | 54 (0.3) |
| OVCAR-5 | 10 (0.05) | 23 (0.1) | 3450 (>15) |
| A1847 | 2.5 (0.015) | 385[c] (2) | 2200 (>10) |
| KB | 15[b] (0.08) | >600 (>3) | >250 (>1) |

[a]If not otherwise mentioned, these values are mean values of at least two experiments.
[b]Results from one experiment.
[c]Non-specific toxicity.

EXAMPLE VII

Clearance of Recombinant Ricin Toxin A (rRTA) Chain Conjugates from the Blood

The clearance of rRTA conjugates and RTA conjugates was compared as follows: Two murine monoclonal antibodies designated 280 DII and 520 C9 were used. The production of these antibodies is disclosed in U.S. Patent Application Ser. No. 690,750 filed Jan. 11, 1985 and assigned to the same assignee as the present invention and is herein incorporated by reference. RTA or rRTA was conjugated to the monoclonal antibodies using iminothiolane as described above and the conjugates were suspended in phosphate buffered saline (PBS). Sufficient conjugate was injected in a volume of 0.1 to 0.2 ml into the tail vein of Balb/c female mice weighing approximately 20 9rams each to obtain initial concentrations of conjugate of between 82 and 229 μg RTA conjugate/ml mouse serum and between 80 and 219 μg rRTA conjugate/ml of mouse serum.

The initial serum concentrations were determined as follows. 60 microliters of venous blood was removed from the retroorbital venous plexus at two minutes after injection of the conjugate into the tail vein of each mouse and at two other time points per experiment including 30 minute, three hours, six hours, 24 hours and 72 hours. The blood was obtained using a heparinized capillary tube and were spun in a Beckman microfuge. The plasma was stored at −20° C. until it was assayed in a colorometric cytotoxicity assay and an ELISA assay. The assays were carried out as follows:

1. Cytotoxicity Assay - Cell line MCF-7 was used for the cytotoxicity assay. Each well of a 96-well tissue culture plate (Falcon Plastics #3075) is filled with 50 microliters of a MEM Earles media (Cetus #M4-2) plus 10% fetal calf serum (Flow Laboratories #29101-54) and 1% penicillin-streptomycin at 5000 units-5000 mg/ml (Irvine Scientific #9364). The media can be UV sterilized without the generation of any toxic side effects for the cells.

Twenty-five microliters of each test sample is added to the first well of columns #2 through #11 of the 96-well plate with a maximum of ten test samples per plate. Sarples are then serially diluted 1:3 to the end of each column with the remaining 25 microliters being discarded.

Plates are then UV sterilized for 10 minutes at 100 $\mu W/CM^2$.

MCF7 cell suspensions are prepared at a concentration of $1 \times 10^5$ cells/ml. One-hundred microliters of cell suspension is added to all wells of the 96-well plates, using either a manual or automated 8-prong dispensing manifold.

Control wells are as follows: The eight wells of the #12 column are used as a maximum absorbance for the plate (this column being corposed of cells and media only). The first column of each plate is used as the minimum absorbance reading for the plate, and also is used to blank the optical reader (Tierteck Multiscan). Each well of the first column receives 20 microliters of a 1:100 dilution of 1 mg/ml whole ricin toxin solution to kill all of the cells in the well. (Final concentration of 0.2 $\mu$g per well.)

Plates are placed in the incubator but not stacked upon each other. This results in more uniform growth of cells in all the wells of each plate. Plates are incubated for 72 hours at 37° C. and 6% CO2

After the 72-hour incubation, 60 microliters of a 1:4 dilution of 5 mg/ml stock 3-(4,5-dimethylthiazoyl-2-yl)-2,5 diphenyl tetrazolium bromide (MTT) solution Sigma (#M-2128) is added to each well of the assay plates.

Plates are reincubated for four-six hours at 37° C. and 5% $CO_2$.

After the incubation period, all medium is aspirated from each well of the assay plates and 150 microliters of a 3% SDS-0.04 normal HCL-isopropanol mixture is added to each well. The acidalcohol mixture solubilizes the formazan crystals produced from the MTT and the SDS prevents precipitation of any residual serum proteins. Plates are left at room temperature for 30-60 minutes to allow the color to develop.

Plates are then read at 570 nm using a Tiertek Multiscan plate reader.

A linear correlation between the uptake and reduction of MTT and cell density was shown as follows: MCF-7 cells were serially (two-fold) diluted across a 96-well plate and four identical plates were prepared. Two were selected for treatment with MTT and viable cell counts were done on the remaining two plates. The reduction of MTT correlate with cell density and follows a linear relationship and correlation between observed cell number and expected cell number is good in the range above 1000 cells per milliliter of suspension.

The MTT reduction assay was used to determine the potency and efficacy of serially diluted ricin toxin in a 96-well plate, using MCF-7 cells in a three day assay as described above. The data show a dose dependent killing of MCF-7 cells by the ricin toxin.

To obtain the $TC1D_{50}$, the maximum absorbance control (cells and media only) is set at 100% and all test sample percentages are calculated from this number. A dose response curve for each sample is constructed and a least squares line is determined through the linear portion of the curve. A linear regression equation is then calculated from which the 50% cytotoxicity dilution point is derived. The 50% cytotoxicity dilution point is then multiplied by any predilutions so that a final $TC1D_{50}$ dilution point is determined. This number is used to calculate the $TCID_{50}$ in nanomolar and in micrograms per milliliter.

2. ELISA Assay - Microtiter plates (Dynatech Laboratories) are coated by incubation for one hour at room temperature with 50 $\mu$l/well of 5 $\mu$g/ml rabbit anti-RTA. After the incubation, the plates are washed twice in PBS+1% BSA. The plates are then blocked with 200 $\mu$l/well of PBS+10% fetal calf serum (Hyclone Laboratories) for one hour at room temperature. Following the block, 50 $\mu$l/well of various dilutions of conjugate and the plasma obtained as described above, are added (as well as unconjugated antibody and RTA as negative controls) and incubated for one hour at room temperature. The plates were then washed three times in PBS+BSA. The mouse antibody was detected by 50 $\mu$/l well of 0.01 mg/ml peroxidase-conjugated rabbit anti-mouse antibody (Zymed Laboratories) and incubated at room temperature for one hour. The plates are washed three times in PBS. 200 $\mu$l/well of 2,2azinodi(3 ethylbenzthiazoline sulfonic acid (ABTS) substrate plus 0.5 $\mu$l hydrogen peroxide per ml of ABTS) was added for color development. OD 405 nm was read at various time points. Recombinant RTA and RTA obtained from caster beans, were compared in the ELISA assay using the rabbit anti-RTA polyclonal antibody and were determined to give the same signal.

The percent injected dose in plasma at two minutes is the product of the immunotoxin concentration in plasma at two minutes x 0.7 ml (the estimated plasma volume of a 20 g female mouse) x 100 disclosed by the initial dose of conjugate injected.

The following Table 14 summarizes the results.

TABLE 14

Plasma Clearance of Immunotoxins

| Conjugates | % injected dose in plasma at 2 min. | % initial concentration at 24 hr. compared to 2 min. | Assay |
|---|---|---|---|
| 280D11-IT-rRTA | 70 | 27 ± 20 | Cytotoxicity |
| 280D11-IT-rRTA | 100 | 19 ± 8 | Cytotoxicity |
| 280D11-IT-rRTA | 60 | 12 ± 5 | Cytotoxicity |
| 280D11-IT-RTA | 70 | 1 ± .2 | Cytotoxicity |
| 280D11-IT-RTA | 100 | .4 ± .2 | Cytotoxicity |
| 520C9-IT-RTA | 100 | .1 ± .3 | Cytotoxicity |
| 280D11-IT-E2 | 64 | .9 ± 1 | Cytotoxicity |
| 280D11-IT-E1 | 8 | 0 | Cytotoxicity |
| 280D11-IT-rRTA | 100 | 6.5 ± 2 | ELISA |
| 280D11-IT-rRTA | 70 | 11 ± 2 | ELISA |
| 280D11-IT-RTA | 100 | 2 ± 1 | ELISA |

In addition, FIG. 1 is a graph of the % of initial conjugate plasma concentration remaining at ½ hour, three hours, six hours and 24 hours after injection into Balb/c mice.

The results clearly show that conjugates of recombinantly produced RTA are cleared more slowly from the ciruclation than the corresponding conjugate made with native RTA which is obtained from caster beans. In addition, the lack of a difference in plasma clearance for different antibody native RTA conjugates strongly suggests that properties of the binding ligand play a major role in clearance of conjugates of ricin toxin A from the circulation.

Samples of the hybridomas that produce the monoclonal antibodies from which the immunotoxins according to the invention are derived have been deposited in the American Type Culture Collection or the Collections of In Vitro International under the following accession numbers:

| Hybridoma | Accession No. |
| --- | --- |
| ATCC | |
| 2G3 | HB 8491 |
| 280D11 | HB 8487 |
| 266B2 | HB 8486 |
| 245E7 | HB 8489 |
| 317G5 | HB 8485 |
| 369F10 | HB 8682 |
| 454C11 | HB 8484 |
| 788G6 | HB 8692 |
| 33F8 | HB 8697 |
| 260F9 | HB 8488 |
| 520C9 | HB 8696 |
| In Vitro International Collection | |
| 9C6 | IVI 10056 |
| 44B2 | IVI 10068 |
| 44F4 | IVI 10058 |
| 120H7 | IVI 10061 |
| 200F9 | IVI 10062 |
| 204F4 | IVI 10071 |
| 219F3 | IVI 10072 |
| 388D4 | IVI 10065 |
| 421E8 | IVI 10064 |

| Hybridoma | Accession No. |
| --- | --- |
| 871E3 | IVI 10084 |
| 451C3 | IVI 10081 |
| 650E2 | IVI 10083 |
| 454A12 | IVI 10075 |

These deposits were made under the Budapest Treaty and will be maintained and made accessible in accordance with the provisions thereof.

What is claimed is:

1. A conjugate comprising unglycosylated recombinant ricin toxin A chain and a murine monoclonal antibody, said conjugate being maintained in an effective cytotoxic amount in the circulation of a host animal for substantially longer times than similar conjugates made of native ricin A chain, wherein said monoclonal antibodies are selected from the gorup consisting of 2G3, 9C6, 33F8, 44B2, 44F4, 120H7, 200F9, 204F4, 219F3, -245E7, 260F9, 266B2, 280D11, 317G5, 369F10, 388D4, 421E8, 451C3, 454A12, 454C11, 650E2, -788G6, and 871E3.

2. The conjugate as described in claim 1, wherein said conjugates have the property of being cleared about nine times slower from the circulation of a host animal than conjugates made of native ricin A chain.

* * * * *